(12) United States Patent
Sörensen

(10) Patent No.: US 7,709,003 B2
(45) Date of Patent: May 4, 2010

(54) METHOD OF PRODUCING AN HIV-1 IMMUNE RESPONSE

(75) Inventor: Birger Sörensen, Skien (NO)

(73) Assignee: Bionor Immuno AS, Skien (NO)

( * ) Notice: Subject to any disclaimer, the term of this patent is extended or adjusted under 35 U.S.C. 154(b) by 101 days.

(21) Appl. No.: 11/865,106

(22) Filed: Oct. 1, 2007

(65) Prior Publication Data

US 2008/0107669 A1  May 8, 2008

Related U.S. Application Data

(62) Division of application No. 10/659,324, filed on Sep. 11, 2003, now Pat. No. 7,311,915, which is a division of application No. 09/674,674, filed as application No. PCT/NO00/00075 on Mar. 2, 2000, now Pat. No. 6,706,859.

(30) Foreign Application Priority Data

Mar. 4, 1999 (NO) .................................. 19991078

(51) Int. Cl.
*A61K 39/38* (2006.01)
*A61K 39/12* (2006.01)
*A61K 39/21* (2006.01)
*C12Q 1/00* (2006.01)
*C12Q 1/70* (2006.01)
*G01N 33/53* (2006.01)
*A61K 38/00* (2006.01)

(52) U.S. Cl. .............. 424/188.1; 424/184.1; 424/186.1; 424/187.1; 530/300; 435/4; 435/5; 435/7.1

(58) Field of Classification Search ........................ None
See application file for complete search history.

(56) References Cited

FOREIGN PATENT DOCUMENTS

| DE | 3711016 | 10/1987 |
|---|---|---|
| EP | 0 230 222 | 7/1987 |
| EP | 0 270 114 | 6/1988 |
| EP | 0 307 149 A2 | 3/1989 |
| EP | 0 356 007 | 2/1990 |
| GB | 2 188 639 | 10/1987 |
| WO | WO91/13360 | 9/1991 |
| WO | WO94/28871 | 12/1994 |
| WO | WO95/11255 | 4/1995 |
| WO | WO96/27013 | 9/1996 |
| WO | WO98/40744 | 9/1998 |

OTHER PUBLICATIONS

Derosiers. Prospects for an AIDS vaccine. Nature Medicine Mar. 2004, vol. 10, No. 3, p. 221-223.*
Leslie et al. HIV evolution: CTL escape mutation and reversion after transmission. Nature Medicine Mar. 2004 vol. 10, No. 3, pp. 282-289.*
Altman et al. HIV escape: there and back again. Nature Medicine Mar. 2004 vol. 10, No. 3, p. 229-230.*
Friedrich et al. Reversion of CTL escape—variant immunodeficiency viruses in vivo. Nature Medicine Mar. 2004 vol. 10, No. 3, p. 275-281.*
Tonini et al. Current approaches to developing a preventative HIV vaccine. Current Opinion in Investigational Drugs 2005, vol. 6, No. 2, p. 155-162.*
Haigwood, Predictive Value of Primate Models for AIDS. AIDS Reviews 2004, vol. 6, p. 187-198.*
Puls et al. Therapeutic vaccination against HIV: current progress and future possibilities. Clinical Science 2006, vol. 110, p. 59-71.*
Cruse, J.M. and Lewis, R.E. Illustrated Dictionary of Immunology, 2nd Ed., Boca Raton, Florida, CRC Press LLC, 2003, p. 613.*
Levine, A.J. Why do we not yet have a human immunodeficiency virus vaccine? Journal of Virology, Dec. 2008, vol. 82, No. 24, pp. 11998-12000.*
Klein et al. Examination of the contributions of size and avidity to the neutralization mechanisms of the anti-HIV antibodies b12 and 4E10. Proceedings of the National Academy of Sciences of the United States of America Apr. 16, 2009, electronic publication Early Edition.*
Letvin. Progress toward an HIV vaccine. Annual Review of Medicine 2005, vol. 56, p. 213-223.*
Journal of Virology, vol. 73, No. 1, Jan. 1999, Kavita S. Lole et al., "Full-length Human Immunodeficiency Virus Type 1 Genomes from Subtype C-Infected Seroconverters in India, with Evidence of Intersubtype Recombination," pp. 152-160, see locus AAD12087 a.a. 164-182.
Nature, vol. 354, Dec. 1991, Rodney E. Phillips et al., "Human Immunodeficiency virus genetic variation that can escape cytotoxic T cell recognition," pp. 453-459, table 1, p. 24 res 255-271.
Human Retroviruses and AIDS, Bette Korber et al., "Protein Alignment Summary Table (Gag)," II-A-1 to II-A-15, Dec. 1997.
Virology, vol. 2, Jun. 1994, Gabriel Zwart et al., "Antibody Resonses to HIV-1 Envelope and GAG Epitopes in HIV-1 Seroconverters with Rapid versus Slow Disease Progression," pp. 285-293.
Proceedings of the National Academy of Sciences, vol. 91, No. 23, Nov. 8, 1994, Douglas F. Lake et al. "Autoantibodies to the α/β T-cell receptors in human immunodeficiency virus infection: Dysregulation and mimicry," pp. 10849-10853.
Clinical and Experimental Immunology, vol. 87, No. 1, Jan. 1992, S.J.D. Bell et al., "Definition of an immunodominant T cell epitope contained in the envelope gp41 sequence of HIV-1," pp. 37-45.

(Continued)

*Primary Examiner*—Larry R Helms
*Assistant Examiner*—Louise Humphrey
(74) *Attorney, Agent, or Firm*—Fitzpatrick, Cella, Harper & Scinto

(57) ABSTRACT

The present invention comprises novel and modified peptides capable of inducing an HIV-1 specific immune response without antagonizing the cytotoxic T-cell activity in order to achieve an effective prophylactic and therapeutic vaccine against HIV. The peptides are based on conserved regions of HIV gag p24 proteins. Antigens in free- or carrier-bound form comprising at least one of the said peptides, vaccine compositions containing at least one of the antigens, immunoassay kits and a method of detecting antibodies induced by HIV or HIV specific peptides using such antigens, are described.

15 Claims, No Drawings

OTHER PUBLICATIONS

Nature, vol. 369, No. 6479, Jun. 2, 1994, Paul Klenerman et al., "Cytotoxic T-cell activity antagonized by naturally occurring HIV-1 Gag variants," pp. 403-407.

Nature, vol. 369, No. 6479, Jun. 2, 1994, Antonio Bertoletti et al., "Natural variants of cytotoxic epitopes are T-cell receptor antagonists for antiviral cytotoxic T cells," p. 407.

Immunology and Cell Biology, vol. 72, issue 6, Dec. 1994, Gordon Ada, "Twenty years into the saga of MHC-restriction," pp. 447-454.

Journal of Immunology, vol. 147, No. 5, Sep. 1, 1991, R.P. Johnson et al., "HIV-1 gag-Specific Cytotoxic T Lymphocytes Recognize Multiple Highly Conserved Epitopes" "Fine Specificity of the gag-Specific Response Defined by Using Unstimulated Peripheral Blood Mononuclear Cells and Cloned Effector Cells," pp. 1512-1521.

Science, vol. 278, Nov. 21, 1997, Eric S. Rosenberg et al. "Vigorous HIV-1-Specific CD4+ T Cell Responses Associated with Control of Viremia," pp. 1447-1450.

Novelty Search Report issued by the Hungarian Patent Office on Feb. 27, 2002 in counterpart Hungarian application (i.e., P0200265).

Riffkin et al., "A single amino-acid change between the antigenically different extracellular serine proteases V2 and B2 from Dichelobacter nodosus", Gene, vol. 167 (1995), pp. 279-283.

Abaza et al., "Effects of amino acid substitutions outside an antigenic site on protein binding to monoclonal antibodies of predetermined specifically obtained by peptide immunization", Journal of Protein Chemistry, vol. 11, No. 5 (1992), pp. 433-444.

Cruse et al., Illustrated Dictionary of Immunology (Boca Raton, FL, CRC Press, Inc., 1995), p. 309. QR180.4.C78.

Paul, Fundamental Immunology, (Philadelphia & New York, Lippincott-Raven Publishers, 1993), pp. 250 and 1311-1312. QR181. F84.

Cohen et al., "Pronounced acute immunosuppression in vivo mediated by HIV Tat challenge", Proceedings of the National Academy of Sciences of the United States of America, vol. 96, Issue 19 (Sep. 14, 1999), pp. 10842-10847.

Fox, "No winners against AIDS", Bio/Technology, vol. 12 (Feb. 1994), p. 128.

* cited by examiner

METHOD OF PRODUCING AN HIV-1 IMMUNE RESPONSE

CROSS REFERENCE TO RELATED APPLICATIONS

This application is a divisional of U.S. application Ser. No. 10/659,324, filed on Sep. 11, 2003, which is a divisional of U.S. application Ser. No. 09/674,674, which is a United Sates national stage filing under 35 U.S.C. §371 of International Application No. PCT/NO00/00075, filed on Mar. 2, 2000, which claims the benefit of priority under 35 U.S.C. §119 of Norwegian patent Application No. 19991078, filed on Mar. 4, 1999, all of the above mentioned applications herein incorporated by reference.

BACKGROUND OF THE INVENTION

1. Field of the Invention

The present invention relates to novel peptides based on conserved regions of HIV gag p24, antigens in free or carrier-bound form comprising at least one of the said peptides, vaccine compositions containing at least one of the antigens, immunoassay kits and a method of detecting antibodies, induced by human immunodeficiency virus (HIV) or HIV-specific peptides, using such antigens.

2. Description of Related Art

There is an urgent need to control the global epidemic of HIV infection and the development of a vaccine against HIV is one of the major objectives in AIDS research. In general vaccines should activate antigen presenting cells, overcome genetic restriction in T-cell responses and generate T- and B-memory cells. The variability of the viral population poses a further difficulty in obtaining an effective HIV vaccine. A breakthrough in the ongoing attempts to develop a vaccine against AIDS has so far not been reported. It is now generally accepted that an induction of antigen-specific humoral and cell-mediated immunity is crucial for a development of an effective prophylactic and therapeutic vaccine. All three arms of the immune system including neutralizing antibodies; CD8+CTL and T-helper-1 (TH1) cells might be required for protective immunity to HIV. It is known that CTL can clear other viral infections (Ada, Immunol. Cell Biol., 72:447-454, 1994) and that CTL can lyse infected targets early in infection before viral progeny can be produced and released by cell lysis, Ada et al., supra. The focus has been on selection of antigens as well as on design and evaluation of different adjuvances. The antigens used in different in vitro and in vivo studies have all been from crude proteins to various synthetic peptides, mainly from gp160 and to some extent from p24. A large number of studies have been done on the V3 loop of gp120. Induction of both B- and T-cell responses have been observed; however, it has been reported from an in vitro study that a peptide from the conserved region of gp41 has indicated infection enhancement (Bell S. J., et al., Clin. Exp. Immunol., 87 (1): 37-45, (January 1992).

Naturally occurring HIV sequences in vaccine candidates are not capable of stimulating a stable immune response due to the virus's inherent ability to hide by changing the appearance of the epitopes presented on the cell surface of infected cells. The immune system is fooled into believing that a particular amino acid sequence is relevant when in fact the amino acid of importance is hidden.

A recent study of titers of antibodies against the gag p24 protein, has shown that slow progression towards development of AIDS is associated with high titers, while fast progression towards development of AIDS is associated with low titers. It is shown that persons with low p24 antibody titer develop significantly faster AIDS than persons with high p24 antibody titers (Zwart G., et al. Virology, 201, p. 285-93, June 1994), indicating that p24 can play a key role to control the development of AIDS.

New HIV p24 peptides are described in WO91/13360, wherein the peptides are used in a method of discriminating between a false and true diagnosed HIV-positive serum sample.

Johnson R. P., et al., The Journal of Immunology, Vol. 147, p. 1512-1521, No. 5, Sep. 1, 1991 describe an analysis of the fine specialty of gag-specific CTL-responses in three HIV-1 seropositive individuals. The gag-specific CTL-responses were found to be mediated by CD3+CD8+ lymphocytes which are HLA class I restricted.

EP-A-0 356 007 discloses antigenic determinants, in particular it relates to synthetic polypeptide sequences which are related to proteins present in the HIV-1 and which can be used as a basis for a potential vaccine against AIDS.

Rosenberg E. S. et al., Science, Vol. 278, 21 Nov. 1997, p. 1447-1450 describe that virus specific CD4+ T helper lymphocytes are critical to the maintenance of effective immunity in a number of chronic viral infections, but are characteristically undetectable in chronic human immunodeficiency virus-type 1 (HIV-1) infection. HIV-1 specific proliferative responses to p24 were inversely related to viral load. They conclude that the HIV-1-specific helper cells are likely to be important in immunotherapeutic interventions and vaccine development.

EP 0 230 222, EP 0 270 114, DE 37 11 016 and GB 2 188 639 all in the name of F. Hoffmann-La Roche & Co. Aktiengesellschaft concern recombinant expression and purification of an HTLVIII Gag/Env gene protein or fusion proteins. The proteins consisting of native sequences can be purified to homogeneity and used as a basis for diagnostic tests for detection of antibodies against viruses associated with AIDS. The gag/env protein may also be formulated for use as a vaccine for protection against AIDS through prophylactic immunization.

From a diagnostic and therapeutic point of view, the major problem with using p24 as part of an assay or therapy is associated with the high number of epitopes on p24 which stimulates production of a large number of antibodies with poor specificity, which through repeated boostering on potential mutated sequences can create autoantibodies (Autoantibodies to the alfa/beta T-cell receptors in HIV infection; dysregulation and mimicry. Lake D. F., et al., Proc. Natl. Acad. Sci. USA, (23): 10849-53, Nov. 8, 1994). Further, it is reported that the p24 antibody titer does not reach the same high levels as for the envelope proteins (gp120 and gp41). Normally antibodies to p24 are developed in the early phase of the infection, but the titer is fairly quickly stabilized after the initial infection period. Later the p24 titer gradually decreases while the opposite happens with gp160. These findings can also be seen in relation to recent reports stating that cytotoxic T-cell activity is antagonized by naturally occurring HIV-1 gag variants (Klenerman P., et al., Nature, 2:369 (6479), p. 403-407, 2 Jun. 1994). This can be one of the reasons why a rapid stabilization of the p24 titer is seen and why it later starts to decrease.

Based on the above background data, we decided to investigate the possibility of designing novel synthetic peptides which can mimic the p24 epitope without antagonizing the cytotoxic T-cell activity, in order to meet the need for an effective prophylactic and therapeutic vaccine.

The initial work was based on one epitope which was published by Korber B., et al., Human Retroviruses and AIDS 1997 Eds. Theoretical Biology and Biophysics Group, Los Alamos National Laboratory, Los Alamos, N. Mex. The amino acid sequence of this epitope (203-222) was:

K A L G P G A T L E E M M T A C Q G V G    (SEQ ID NO: 26)

R R M R T K    S I K D    L S S S    R    R    (SEQ ID NO: 27)

G      V R             V    (SEQ ID NO: 28)

S      A A    (SEQ ID NO: 29)

S E    (SEQ ID NO: 30)

Q Q    (SEQ ID NO: 31)

The one letter as well as the three letter codes defining the amino acids in the sequences given throughout this specification are in accordance with International standards and given in textbooks, for instance Lehninger A. L., <<Principles of Biochemistry>>, Worth Publishers Inc., New York, 1982. The amino acids given below the head sequence represent the natural variation of the sequence. An initial study of a sequence containing this modified epitope was conducted on the sequence:

ANPDCKQILKSLGPGATLEEXXTACQGVG-NH$_2$    (SEQ ID NO: 32)

wherein X indicates 2-aminohexanoic acid, and the cysteine residues are in an oxidized state, i.e. are forming an intrachain disulphide bridge. The results (unpublished) from studies using this peptide as part of a diagnostic kit showed that the specificity became 87% (n=279) on a preselected panel of African sera. The sensitivity was surprisingly 100% on a panel of HIV-1 positive sera including HIV-1 subtype O sera, which is quite different from the other subtypes.

In order to improve specificity, i.e. define the amino acids which contribute to a pure non-crossreacting antibody response, a similar study was applied to a significantly shorter and further modified peptide:

LIWGATCQEHXTACQGVG-NH$_2$    (SEQ ID NO: 33)

wherein X has the above-mentioned meaning and the cysteine residues are forming an intrachain disulphide bridge.

The results from this study showed that the specificity of the assay increased to 96%, and (n=293) which is similar to the specificity obtained in the assay without using the p24 peptide. With a specificity of 87% to the assay where the first peptide was included, it would be likely that the peptide would induce an immune response to more than one epitope since it was recognized by unspecific antibodies, if it was used as a vaccine candidate. The latter, however, shows that the peptide sequence is picking up an immune response which is unique to HIV-1. Consequently, if a sequence based on this is used as an antigen in a vaccine candidate, it would most likely boost a unique immune response to HIV-1.

To further increase the number of T-cell epitopes and reduce the probability for development of escape mutants, three additional peptide sequences were based on the following three sequences from residues 264-284, 253-271 and 166-186, respectively, published in Human Retroviruses and AIDS 1997; A Compilation and Analysis of Nucleic Acid and Amino Acid Sequences, Eds. Theoretical Biology and Biophysics Group, Los Alamos National Laboratory, Los Alamos:

```
R W I I L G L N K I V R M Y S P T S I L D   (SEQ ID NO: 34)
K G V V M         M   K     C   V G     E    (SEQ ID NO: 35)
D   M   V         V         Q   I       G    (SEQ ID NO: 36)
                                S            (SEQ ID NO: 37)
                                A            (SEQ ID NO: 38)
N N P P I P V G E I Y K R W I I L G L        (SEQ ID NO: 39)
S   Q A V     K D M L R K G M V M            (SEQ ID NO: 40)
G   G S N       K V     D   V   V            (SEQ ID NO: 41)
H     G T                                    (SEQ ID NO: 42)
A                                            (SEQ ID NO: 43)
P                                            (SEQ ID NO: 44)
and
P E V I P M F S A L S E G A T P Q D L N T    (SEQ ID NO: 45)
  R I T T T L T E   A D     I S Y N I Y M    (SEQ ID NO: 46)
```

-continued

```
L N        A L          V   H   V   I    (SEQ ID NO: 47)
           M            L           A    (SEQ ID NO: 48)
                                    V    (SEQ ID NO: 49)
```

Several modified peptides have been synthesized in order to determine unique sequences which are both specific and sensitive towards HIV-1.

DESCRIPTION OF THE INVENTION

The peptides according to the invention originate from the four different conserved areas of the HIV-1 core protein p24 which are described above, having the properties of maintaining the uniqueness (sensitivity and specificity) of the HIV-1-epitope. Further, the new peptides according to the invention possess no recognized cytotoxic T lymphocyte (CTL) antagonistic effect and shall have at least one potential CTL epitope.

The peptides, according to the invention, which have met the above criteria are selected from the following groups;

(SEQ ID NO: 1)

Xaa$_1$ Xaa$_2$ Xaa$_3$ Xaa$_4$ Xaa$_5$ Xaa$_6$ Ala Xaa$_8$ Xaa$_9$ Gln

Thr Pro Trp Xaa$_{14}$ Xaa$_{15}$ Xaa$_{16}$ Xaa$_{17}$ Xaa$_{18}$ Val

Xaa$_{20}$ wherein the amino acids of the chain could have the following meanings;

Xaa in position 1 of the peptide derivate is Lys or Arg,
Xaa in position 2 is Ala, Gly, Ser or Arg,
Xaa in position 3 is Leu or Met,
Xaa in position 4 is Gly or Arg,
Xaa in position 5 is Pro, Thr, Val, Ser, Gln or Ala,
Xaa in position 6 is Gly, Ala, Lys, Arg, Gln or Glu,
Xaa in position 8 is Thr or Ser,
Xaa in position 9 is Leu or Ile,
Xaa in position 14 is Thr, Ser or Val,
Xaa in position 15 is Ala or Ser,
Xaa in position 16 is Cys or Ser,
Xaa in position 17 is Gln or Leu
Xaa in position 18 is Gly, Glu or Arg,
Xaa in position 20 is Gly or Arg, the peptide comprises at least nine consecutive amino acids of the sequence of SEQ ID NO: 1, (SEQ ID NO: 4)

Xaa$_1$ Xaa$_2$ Xaa$_3$ Xaa$_4$ Xaa$_5$ Gly Leu Asn Pro Leu Val

[Gly]$_n$ Xaa$_{12}$ Xaa$_{13}$ Tyr Xaa$_{15}$ Pro Xaa$_{17}$ Xaa$_{18}$ Ile

Leu Xaa$_{21}$ Xaa$_{22}$ wherein the amino acids of the chain have the following meaning;

Xaa in position 1 is Arg, Lys, Asp or none
Xaa in position 2 is Trp, Gly, Lys or Arg,
Xaa in position 3 is Ile, Leu, Val or Met
Xaa in position 4 is Ile, Val or Leu
Xaa in position 5 is Leu, Met, Val or Pro
Xaa in position 12 is Arg, Lys
Xaa in position 13 is Met or Leu,
Xaa in position 15 is Ser, Cys or Gln,
Xaa in position 17 is Thr, Val, Ile, Ser or Ala,
Xaa in position 18 is Ser, Gly or Thr,
Xaa in position 21 is Asp, Glu, Cys or Gly,
Xaa in position 22 is Gly or none wherein the sequence of SEQ ID NO: 4 comprises at least six consecutive amino acids and n=0, 1, 2 or 3, (SEQ ID NO: 9)

Xaa$_1$ Xaa$_2$ Xaa$_3$ Pro Ile Pro Xaa$_7$ Xaa$_8$ Xaa$_9$ Xaa$_{10}$

Xaa$_{11}$ Xaa$_{12}$[Gly ]$_n$ Xaa$_{13}$ Xaa$_{14}$ Xaa$_{15}$ Xaa$_{16}$ Xaa$_{17}$

Xaa$_{18}$ Xaa$_{19}$ Xaa$_{20}$ Xaa$_{21}$ Xaa$_{22}$ Xaa$_{23}$ Xaa$_{24}$ wherein Xaa in position 1 is Asn, Ser, Gly, H is, Ala, Pro, Arg or none Xaa in position 2 is Asn, Ala or Lys
Xaa in position 3 is Pro, Gln, Gly, Ile or Leu
Xaa in position 7 is Val or Ala
Xaa in position 8 is Gly or Lys
Xaa in position 9 is Glu, Asp, Lys, Phe or Thr
Xaa in position 10 is Ile, Met, Val or Leu
Xaa in position 11 is Tyr, Leu or none
Xaa in position 12 is Ser or none
Xaa in position 13 is Arg or none
Xaa in position 14 is Asp, Arg, Trp, Ala or none
Xaa in position 15 is Ile or none
Xaa in position 16 is Tyr or none
Xaa in position 17 is Lys or Arg
Xaa in position 18 is Arg, Lys or Asp
Xaa in position 19 is Trp or Gly
Xaa in position 20 is Ile, Met, Val, Gln or Ala
Xaa in position 21 is Ile, Val or Ala
Xaa in position 22 is Leu, Met or Val
Xaa in position 23 is Gly or Cys
Xaa in position 24 is Leu or none wherein the sequence of SEQ ID NO: 9 consists of at least six consecutive amino acids and n=1, 2 or 3, (SEQ ID NO: 15)

Xaa$_1$ Xaa$_2$ Ile Ile Xaa$_5$ Xaa$_6$ Xaa$_7$ Xaa$_8$ Xaa$_9$ Leu

Xaa$_{11}$ [Gly]$_n$ [Arg]$_m$ Xaa$_{12}$ Xaa$_{13}$ Xaa$_{14}$ Xaa$_{15}$ Xaa$_{16}$

Xaa$_{17}$ Xaa$_{18}$ Xaa$_{19}$ Xaa$_{20}$ Xaa$_{21}$ Xaa$_{22}$ Xaa$_{23}$ Xaa$_{24}$

Xaa$_{25}$ wherein the Xaa in position 1 is Pro, Lys, Arg or none

Xaa in position 2 is Glu, Arg, Phe or Lys
Xaa in position 5 is Pro or Thr
Xaa in position 6 is Met, Thr or Nleu
Xaa in position 7 is Phe or Leu
Xaa in position 8 is Ser, Thr, Ala or Met
Xaa in position 9 is Ala, Glu or Leu
Xaa in position 11 is Ser or none
Xaa in position 12 is Ala, Arg or none
Xaa in position 13 is Ile, Leu or none
Xaa in position 14 is Ser, Ala, Leu or none
Xaa in position 15 is Tyr, Glu or Asp Xaa in position 16 is Gly or Asp
Xaa in position 17 is Ala or Leu
Xaa in position 18 is Thr, Ile, Val, Leu or Asn,
Xaa in position 19 is Pro, Thr or Ser
Xaa in position 20 is Tyr, Phe, Nleu, H is or Gln
Xaa in position 21 is Asp, Asn, Leu or Ala
Xaa in position 22 is Leu, Ile, Val or Asn
Xaa in position 23 is Asn, Tyr, Cys or Gly
Xaa in position 24 is Thr, Met, Ile, Ala, Val or none
Xaa in position 25 is Gly or none
wherein the sequence of SEQ ID NO: 15 consists of at least six consecutive amino acids, n=1, 2 or 3 and m=0, 1, 2 or 3,
the terminal ends of the sequences may be free carboxyl- or amino groups, amides, acyls, acetyls or salts thereof,
two or more of the Cys residues may form part of an intrachain- or interchain disulphide binding, a —S—$(CH_2)_p$—S— or a —$(CH_2)_p$-bridge wherein p=1-8, optionally intervened by one or more heteroatoms such as O, N or S and/or the said peptide sequences are immobilized to a solid support.

The new peptide sequences have the potential to serve as a good antigen wherein the antigen comprises at least one peptide selected from the group of sequences of SEQ ID NO: 1, SEQ ID NO: 4, SEQ ID NO: 9 or SEQ ID NO: 15. The antigenicity may be adapted through adjusting the ratio or concentration of different peptides or size of the peptides by for instance dimerisation or polymerisation and/or immobilisation to a solid phase. The antigen comprises two or more polypeptide sequences, according to the invention, which are either linked by a bridge for instance a disulphide bridge between the Cys residues of the chains or bridges like $C_1$-$C_8$ alkylen possibly intervened by one or more heteroatoms like O, S, or N or preferably they are unlinked. The chains may be immobilized to a solid phase in monomeric, dimeric or oligomeric forms. Further amino acids may be added to the ends in order to achieve an <<arm>> to facilitate immobilization.

All amino acids in the peptides of the invention can be in both D- or L-form, although the naturally occurring L-form is preferred.

The C- and N-terminals ends of the peptide sequences could deviate from the natural sequences by modification of the terminal $NH_2$-group and/or COOH-group. They may, for instance, be acylated, acetylated, amidated or modified to provide a binding site for a carrier or another molecule.

The peptides according to the invention consist of 6 to 50 amino acids, preferably between 10 and 30 amino acids. They cover all natural variations of amino acids in the identified positions.

The polypeptide antigen according to the invention is either in a free or in a carrier-bound form. The carrier or solid phase to which the peptide is optionally bound can be selected from a wide variety of known carriers. It should be selected with regard to the intended use of the immobilized polypeptide as a diagnostic antigen or as an immunizing component in a vaccine.

Examples of carriers that can be used for diagnostic purposes, for example, are magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatine or polysaccharide particles or other protein particles, red blood cells, mono- or polyclonal antibodies or fab fragments of such antibodies.

According to a further embodiment of the present invention, the antigens may form part of a vaccine possibly combined with carriers, adjuvants or combined with other immunostimulating elements such as canarypox virus carrying the env gene. Examples of carriers and/or adjuvants for vaccine purposes are other proteins such as human or bovine serum albumin and keyhole limpet haemocyanin. Immunostimulatory materials may be divided into three groups; adjuvants, carriers for antigens and vehicles. Examples of adjuvants include aluminum hydroxyd, aluminum salts, saponin, muramyl di- and tri-peptides, monophosphoryl lipid A, *B. pertussis* and various cytokines including the Th1 cytokine IL-12 and 1 L-1. A number of protein toxins can be used to carry passenger proteins across cellular membranes into the cytosol, which are useful in developing CTL vaccines. Carriers include bacterial toxoids such as inactivated tetanus and cholera toxins, genetically detoxified bacterial toxins such as heat labile enterotoxin from *E. coli*, fatty acids, live vectors such as polio chimeras and hybrid proteins that form particulates for example yeast retrotransposon hybrid TY particles and HBcAg particles. Vehicles which are frequently occurring components in modern vaccines are consisting of mineral oil emulsion, Freunds complete and incomplete adjuvant, vegetable oil emulsions, nonionic block co-polymer surfactants, squalene or squalane, liposomes and biodegradable microspheres. Two novel adjuvants which possess significant potential for the development of new vaccines include an oil-in water microemulsion (MF59) and polymeric microparticles. Any substance that can enhance the immunogenicity of the antigen may be used and several further alternatives of carriers or adjuvants are given in the US or European Pharmacopoeia.

A suitable formulation of the antigen for immunostimulatory uses may also comprise interferons such as INF-γ, antiviral chemokines or haematopoietic growth factors such as granulocyte macrophage growth factor.

Another approach in order to enhance the stimulation and absorption in, for instance, the intestine is to administer the peptides of the invention with small peptides such as di- tri- or tetra peptides. These peptides can be administered in addition to or in combination with the peptides of the invention. Preferably the peptides are administered together with the tripeptide YGG, consisting or amino acids in the D- or L-forms, preferably in the D-form.

Recent approaches to non-parenteral delivery of vaccines, for instance, via mucosa include: gene fusion technology to create non-toxic derivatives of mucosal adjuvants, genetically inactivated antigens with a deletion in an essential gene, coexpression of an antigen and a specific cytokine that is important in the modulation and control of a mucosal immune response, and genetic material itself that would allow DNA or RNA uptake and its endogenous expression in the host's cells.

One approach for developing durable responses where cell-mediated immunity is required is to vaccinate with plasmid DNA encoding one or more specific antigen(s).

In order to protect against HIV infection, vaccines should induce both mucosal and systemic immune responses and could be administered by any convenient route, parenterally or non-parenterally, such as subcutaneously, intracutaneously, intravenously, intramuscularly, perorally, mucosally or intranasally, for example.

In a preferred embodiment, the vaccine according to the present invention comprises antigens containing the peptides of the SEQ ID NO: 1, 4, 9 and 15. More preferably the peptides occur in the ratio 1:1:1:1.

In a further preferred embodiment the vaccine composition contains the antigens;

```
                                    (SEQ ID NO: 3)
R A L G P A A T L Q T P W T A S L G V G - NH₂

(SEQ ID NO: 6)
R W L L L G L N P L V G G G R L Y S P T S I L G -
NH₂

(SEQ ID NO: 11)
R A I P I P A G T L L S G G G R A I Y K R T A I L
G - NH₂
and
                                    (SEQ ID NO: 18)
R F I I P NI F T A L S G G R R A L L Y G A T P Y A
I G - NH₂.
```

One of the sequences contains a B-cell epitope and will activate the humoral immune system, whereas the other sequences contribute with CTL-epitopes and the amino acid changes implemented within the frame of the CTL-epitope are designed to achieve enhanced binding. Other amino acid changes have been conducted in order to facilitate the synthesis of the peptide and/or increase the solubility of the peptide.

A method for detecting antibodies, induced by HIV-1 or HIV-1 specific peptides or proteins, in a sample of body fluid using the present antigens is a further embodiment of the invention. Also immunoassay kit designed for this detection and antibodies capable of selectively reacting with the said antigens are encompassed by the present invention.

Description of the Preparation of the Peptides

The peptides of the invention can be produced by any known method of producing a linear amino acid sequence, such as recombinant DNA techniques. A nucleic acid sequence which encodes a peptide of the invention or a multimer of the said peptides, is introduced into an expression vector. Suitable expression vectors are for instance plasmids, cosmids, viruses and YAC (yeast artificial chromosome) which comprise necessary control regions for replication and expression. The expression vector may be stimulated to expression in a host cell. Suitable host cells are for example bacteria, yeast cells and mammal cells. Such techniques are well known in the art and described for instance by Sambrook et al., Molecular Cloning: A Laboratory Manual, Cold Spring Harbor Laboratory Press, Cold Spring Harbor, 1989. Other well-known techniques are degradation or synthesis by coupling of one amino acid residue to the next one in liquid phase or preferably on a solid phase (resin) for instance by the so-called Merrifield synthesis. See for instance Barany and Merrifield in the Peptides, Analysis, Synthesis, Biology, Vol. 2, E. Gross and Meinhofer, Ed. (Acad. Press, N.Y., 1980), Kneib-Coronier and Mullen Int. J. Peptide Protein Res., 30, p. 705-739 (1987) and Fields and Noble Int. J. Peptide Protein Res., 35, p. 161-214 (1990).

In case a linked or cyclic peptide is desired, the amino acid sequence is subjected to a chemical oxidation step in order to cyclize or link the two cysteine residues within one or between two peptide sequences, when the appropriate linear amino acid sequences are synthesized, see Akaji et al., Tetrahedron Letter, 33, 8, p. 1073-1076, 1992.

General Description of Synthesis

All peptide derivatives prepared in the Examples given below were synthesized on a Milligen 9050 Peptide Synthesizer using a standard program. The resin used was Tenta Gel P RAM with a theoretical loading of 0.20 meq/g (RAPP POLYMERE GmbH, Tübingen). The final product of the synthesis was dried in vacuo overnight. The peptide was then cleaved from the resin by treatment with 90% trifluoroacetic acid in the presence of ethandithiol (5%) and water (5%) as scavengers (1.5 hours at RT). Then the resin was filtered and washed on filter with additional trifluoroacetic acid (100%) (2×20 ml). The combined filtrates were evaporated in vacuo (water bath at RT) and the residue was triturated with ethyl ether (200 ml) and the precipitated product filtered off. The solid was promptly dissolved on filter with glacial acetic acid (100 ml) and added 1.5 l of 20% acetic acid in methanol and treated with 0.1 M solution of iodine in methanol until a faint brown colour remained. Then Dowex 1×8 ion exchange in acetate form (15 g) (Bio-Rad, Richmond, Calif.) was added and the mixture filtered. The filtrate was evaporated and the residue freeze-dried from acetic acid. The product was then purified by reversed phase liquid chromotography on a column filled with Kromasil® 100-5 C8 (EKA Nobel, Surte, Sweden) in a suitable system containing acetonitrile in 0.1% trifluoroacetic acid water solution. The samples collected from the column were analyzed by analytical high performance liquid chromatography (HPLC) (Beckman System Gold, USA) equipped with a Kromasil® 100-5 C8 Column (EKA Nobel, Surte, Sweden). Fractions containing pure substance were pooled, the solvent was evaporated and the product freeze-dried from acetic acid. The final HPLC analysis was performed on final product, and the structure of the peptide was confirmed by amino acid analysis and mass spectrometry (LDI-MS).

All amino acids used during the synthesis were L-amino acids and they were protected with a fluorenylmethoxy-carbonyl group at the α-amino function. The side chains were protected as follows:

Cys (Trt), Gln(Trt), Glu(OtBu), Thr(tBu).

The abbreviations, within the brackets are:

Trt=triphenylmethyl t-Bu=tert. Butyl

OtBu=tert. Butylester

The amino acid derivatives was supplied by Bachem A G, Switzerland.

Example 1

(SEQ ID NO: 2)
Preparation of K A L G P G A T L Q T P W T A C Q G

V G - $NH_2$.

The peptide was synthesized in amide form, from corresponding starting materials according to the general description of synthesis. The purity was determined by HPLC analysis and the structure was confirmed by amino acid analysis and mass spectrometry (LDI-MS).

Purity (HPLC): 87%

Example 2

Preparation of (SEQ ID NO: 3)
R A L G P A A T L Q T P W T A S L G V G.

The peptide was synthesized in amide form, from corresponding starting materials according to the general description of synthesis. The purity was determined by HPLC analysis and the structure was confirmed by amino acid analysis and mass spectrometry (LDI-MS).

Purity (HPLC): more than 95%
Molecular weight (free base): 1966
Molecular formula: $C_{88}H_{144}O_{25}N_{26}$

Example 3

Preparation of
(SEQ ID NO: 5)
W I I P G L N P L V G G G K L Y S P T S I L C G-NH$_2$.

The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): 95%
Mass spectral analysis: Theoretical molecular weight: 2454.9
Experimental molecular weight: 2454.8 ES+

Example 4

Preparation of
(SEQ ID NO: 6)
R W L L L G L N P L V G G G R L Y S P T S I L G.

The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 95%
Molecular weight (free base): 2552
Molecular formula: $C_{119}H_{195}O_{29}N_{33}$

Example 5

Preparation of
(SEQ ID NO: 7)
K I L L G L N P L V G G G R L Y S P T S I L G, (SEQ ID NO: 8)
R L L L G L N P L V G G G R L Y S P T T I L G
and (SEQ ID NO: 24)
N I P I P V G D I Y G G G D I Y K R W Q A L C L.

The peptides are synthesized in amide form, from the corresponding starting materials according to the general description of synthesis. The purity are determined by HPLC analysis and the structures are confirmed by amino acid analysis and mass spectrometry (LDI-MS).

Example 6

Preparation of
(SEQ ID NO: 10)
R N I P I P V G D I Y G G G D I Y K R W Q A L C L.

The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): 85%
Mass spectral analysis: Theoretical molecular weight: 2817.3
Experimental molecular weight: 2813.7 ES+

Example 7

Preparation of
(SEQ ID NO: 11)
R A I P I P A G T L L S G G G R A I Y K R W A I L G.

The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 95%
Molecular weight (free base): 2707
Molecular formula: $C_{125}H_{208}O_{29}N_{38}$

Example 8

Preparation of
(SEQ ID NO: 12)
A L P I P A G F I Y G G G R I Y K R W Q A L G, (SEQ ID NO: 13)
K I P I P V G F I G G G W I Y K R W A I L G
and (SEQ ID NO: 14)
K I P I P V G T L L S G G G R I Y K R W A I L G.

The peptides are synthesized in amide form, from the corresponding starting materials according to the general description of synthesis. The purity are determined by HPLC analysis and the structures are confirmed by amino acid analysis and mass spectrometry (LDI-MS).

Example 9

Preparation of
(SEQ ID NO: 16)
K F I I P NI F S A L G G A I S Y D L N T NI L N C I.

The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).

Purity (HPLC): more than 80%
Mass spectral analysis: Theoretical molecular weight: 2783.3
Experimental molecular weight: 2783.3 ES+

Example 10

Preparation of
(SEQ ID NO: 17)
K F I I P NI F S A LS G G G A I S Y D L N T F L N C I G.

The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).

Purity (HPLC): more than 80%

Mass spectral analysis: Theoretical molecular weight: 2932.4

Experimental molecular weight: 2931.8 ES+

Example 11

Preparation of
(SEQ ID NO: 18)
R F I I P NI F T A L S G G R R A L L Y G A T P Y A I G.

The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).

Purity (HPLC): more than 95%

Molecular weight (free base): 2894

Molecular formula: $C_{137}H_{217}O_{32}N_{37}$

Example 12

Preparation of
(SEQ ID NO:19)
K I I P NI F S A L G G G R L L Y G A T P Y A I G, (SEQ ID NO:20)
R I I P NI F T A L S G G G R L L Y G A T P Y A I G
and (SEQ ID NO:25)
W I I P NI F S A L G G A I S Y D L N T NI L N C I.

The peptides are synthesized in amide form, from the corresponding starting materials according to the general description of synthesis. The purity are determined by HPLC analysis and the structures are confirmed by amino acid analysis and mass spectrometry (LDI-MS).

Example 13

Dimerisation Via Disulphide Bridge

The peptide sequences of Examples 1 and 3 were linked via an oxidation step to form a dipeptide wherein the cysteine residues formed a disulphide bridge. The bridge was formed in either of two ways:

A) Oxidation with $I_2$. Equals amounts of the peptides were dissolved in acetic acid methanol (1:4) and 0.1 M $I_2$ in methanol was added yielding a mixture of the dimer.

or

B) Oxidation via [Cys(Spy)$^{16}$]-SEQ ID NO: 2. 2.3 mM of the peptide of SEQ ID NO: 2 dissolved in 2 M AcOH (aq) and 2-propanol (1:1) was treated with 2,2 dithiodipyridin (3 eqv) to yield [Cys(Spy)$^{16}$]-SEQ ID NO: 2. Equal amounts of [Cys (Spy)$^{16}$]-SEQ ID NO: 2 and peptide of SEQ ID NO: 5 were dissolved in 10 mM NH$_4$Oac (aq pH=6.5) and methanol (5:2) to yield the dimer of SEQ ID NO: 21.

The purity of the peptide was determined by HPLC analysis and the peptide structure was confirmed by amino acid analysis. The peptide content (amino acid free base) was 80%, Purity (HPLC): 92%.

Example 14

A vaccine comprising the peptides of the SEQ ID NO: 3, 6, 11 and 18 was prepared. The freeze-dried peptides were dissolved in sterile water at a final concentration of 4 mg/ml. The final salt concentration was 0.9%. A preparation of a granulocyte-macrophage-colony stimulating factor (GM-CSF) was also prepared, according to the manufacturer's directions for use, to a final concentration of 0.3 mg/ml. The two solutions are administered intracutaneously. A typical injection dose is 100 µl.

Example 15

An antigen solution or suspension is mixed with equal parts of Freund's adjuvant of Behring, complete or incomplete, and is then finely emulsified by being drawn up into, and vigorously pressed out of, an injection syringe, or with a homogenator. The emulsion should remain stable for at least 30 minutes. The antigen-adjuvant emulsion is best injected subcutaneously as a depot.

Example 16

Toxicity Data

The dipeptide of Example 13 was diluted in 0.9% NaCl) to a test solution concentration of 4 mg/ml. The peptide was administered by injection to NMFI female mice in a dose of 100 µg per kg bodyweight. No toxicological effects were observed and the peptide was deemed not toxic.

Toxicity studies were performed in mice and rats on the peptide composition of the vaccine in Example 14. The mice were selected for the study to provide comparative data from a second commonly used rodent species. The test substance was a mixture of four peptides supplied in one vial containing lyophilised material for reconstitution with physiological saline, and dose levels were expressed in terms of total peptide load. The individual peptides were present in the ratio 1:1:1:1, giving dose levels of each peptide of 0.0075 mg/kg body weight, 0.075 mg/kg body weight and 0.75 mg/kg body weight, which are up to 500 fold the intended human dose. The test animals were divided into four groups of ten animals each (five males and five females); a saline control group and groups for low, intermediate and high doses. The test composition was administered once, by intravenous infusion into a tail vein at a dose rate of 3 ml/minute. The animals were killed at day 15 and 16 by intraperitoneal injection of sodium pentobarbitone.

The results of these studies indicated that the dose levels administered to the mice and rats elicited no adverse reactions and that the no effect level was in excess of 3 mg/kg.

Example 17

Immunoassay for Detection of Antibodies Induced by HIV-1

The magnetic particle reagents are to be prepared according to the manufacturer's recommended protocol. Dynal AS is the manufacturer of the Dynabeads, which are employed. The magnetic particles coated with ligand are called Reagent 1. A peptide according to the invention is covalently coupled to the pre-activated surface of the magnetic particles. It is also possible to physically absorb the peptide to the surface of the magnetic particles. The concentration of particles in Reagent 1 is within the range from 1 mg/ml to 15 mg/ml. The particle size varies between 0.2 µm to 15 µm. The concentration of peptides is within the range from 0.01 mg/mg particle to 1 mg/mg particle.

The anti human Ig Alkaline Phosphatase (AP) conjugated antibody reagent is prepared according to the recommended protocol of Dako AS. This protocol is a standard procedure in this field. This reagent is called Reagent 2.

The substrate solution phenolphtalein-monophosphate is to be prepared according to the recommended protocol of Fluka AG. This protocol is a standard procedure in this field. The substrate solution is called Reagent 3.

The washing and incubation buffer which is used is standard 0.05M tris-base buffer with the following additional compounds; Tween 20 (0.01% to 0.1%), glycerol (0.1% to 10%) and sodium chloride (0.2% to 0.1%).

The assay procedure comprises an incubation step wherein 1 drop of Reagent 1 is mixed with 2 drops of washing buffer in each well. After mixing, 30 µl of sample is added and the solution is incubated for 5 minutes. The magnetic particles can be trapped by a magnet and the liquid removed, before the magnet is separated. Then the wells are washed twice in 4 drops of washing solution, before incubation with Reagent 2. 1 drop of Reagent 2 is added with 2 drops of washing buffer and the solution is incubated for 5 minutes. The magnetic particles can be trapped by a magnet and the liquid removed, before the magnet is separated. Then the washing step is repeated before incubation with Reagent 3. 2 drops of Reagent 3 is added to each well and the solution is incubated for 3 minutes. The results can be read against a white background. Positive results are red (3+=strong red) whereas negative results are clearly light yellow/brown solutions as obtained in the negative control.

The immunoassay kit could be used in detection of antibodies, induced either by HIV virus or HIV-specific peptides or proteins, for instance the peptides of the present invention.

The above Examples are only meant as illustrating the invention. It must be understood that a person skilled in the art can modify the peptides, antigens and vaccines herein described without deviating from the concept and scope of this invention as set forth in the claims.

The polypeptides of the invention can be used in a combination of at least one peptide selected from each group of sequences, SEQ ID NO: 1, SEQ ID NO: 4, SEQ ID NO: 9 and SEQ ID NO: 15 to form antigens and the active principle of a proplylactic or therapeutic vaccine intended to provide protection against the human immunodeficiency virus type 1 (HIV-1). The vaccine may include compounds having beneficial effects in protecting or stimulating the host's immune system (human being or vertebrate animal) for instance interleukins, interferons, granulocyte macrophage growth factors, haematopoietic growth factors or similar. Preferably the vaccine composition further contains an adjuvant or vehicle, more preferably the adjuvant or vehicle is Monophosphoryl Lipid A (MPL®) possibly with alum, Freund's adjuvant (complete or incomplete) or aluminum hydroxyd. The optimal amount of adjuvant/vehicle will depend on the type(s) which is chosen.

The peptide or vaccine formulation can be freeze-dried prior to storage. The vaccine may be stored preferably at low temperature, in ampoules containing one or more dosage units, ready for use. A typical dosage unit of the peptide according to the invention is within the concentration range: 1 µg-1 mg per kg bodyweight, preferably within 2 µg-0.15 mg per kg bodyweight. Persons skilled in the art will appreciate that a suitable dose will depend on the body weight of the patient, the type of disease, severity of condition, administration route and several other factors. The vaccine might be administered up to twelve times and through injection, typically it will be administered about three times. In preparation of an injection solution the peptides are dissolved in sterile sodium chloride solution at a final concentration of 1 mg/ml per peptide and 0.9% sodium chloride. Typically an injection volume is 100 µl to 200 µl (2×100 µl). The peptide is preferably co-administered with a suitable adjuvant and/or a granulocyte-macrophage growth factor for instance Leucomax® <<Schering Plough>>. Suitable administration may be intracutaneous, subcutaneous, intravenous, peroral, intramuscular, intranasal, mucosal or any other suitable route. Booster administrations may be required in order to maintain protection. For persons skilled in the art it will be understood that the vaccine compositions according to the invention are useful not only in the prevention of infection, but also in the treatment of infection.

What is claimed is:

1. A synthetic peptide comprising the amino acid sequence of SEQ ID NO:4.

2. The synthetic peptide according to claim 1, wherein the amino acid sequence of SEQ ID NO:4 is selected from the group consisting of SEQ ID NO:5, SEQ ID NO:6, SEQ ID NO:7, and SEQ ID NO:8.

3. An antigen comprising at least one synthetic peptide according to claim 1.

4. The antigen according to claim 3, comprising at least one synthetic peptide selected from the group consisting of SEQ ID NO:5, SEQ ID NO:6, SEQ ID NO:7, and SEQ ID NO:8.

5. An immunogenic composition comprising the antigen according to claim 3, a pharmaceutically acceptable diluent, optionally an adjuvant, a carrier and/or vehicle, and optionally one or more additional immunostimulatory compounds.

6. The immunogenic composition according to claim 5, wherein the antigen comprises at least one synthetic peptide selected from the group consisting of SEQ ID NO:5, SEQ ID NO:6, SEQ ID NO:7, and SEQ ID NO:8.

7. The immunogenic composition according to claim 6, wherein the antigen comprises the synthetic peptide of SEQ ID NO:6.

8. The immunogenic composition according to any one of claims 5-7, wherein the synthetic peptide is dissolved in a saline water solution and the optional one or more immunostimulatory compounds include a granulocyte macrophage growth factor.

9. The immunogenic composition according to any one of claims 5-7, wherein the immunogenic composition comprises an adjuvant selected from the group consisting of monophosphoryl lipid A, Freund's complete adjuvant, Freund's incomplete adjuvant, and aluminum hydroxide.

10. A method of detecting antibodies induced by an HIV particle, HIV-specific peptides, or HIV proteins in a sample of body fluid, comprising the step of subjecting the sample to an immunoassay utilizing at least one antigen, wherein the antigen comprises at least one synthetic peptide selected from the group consisting of synthetic peptides recited in any one of claim 1 or claim 2.

11. An immunoassay kit for the detection of antibodies induced by an HIV particle, HIV-specific peptides, or HIV proteins in a sample of body fluid, wherein the kit comprises a diagnostic antigen that is the synthetic peptide of claim 1 or 2.

12. The synthetic peptide of claim 1, wherein the terminal ends of the synthetic peptide are selected from the group consisting of free carboxyl or amino groups, amides, acyls, acetyls, and salts thereof.

13. The synthetic peptide of claim 1, wherein two or more Cys residues form part of an intrachain or interchain disulphide bond.

14. The synthetic peptide of claim 1, wherein two or more Cys residues form a —S—$(CH_2)_p$—S— or a —$(CH_2)_p$-bridge wherein p=1-8, optionally intervened by one or more heteroatoms selected from the group consisting of O, N, and S.

15. The synthetic peptide of claim 1, wherein the synthetic peptide is immobilized to a solid support.

* * * * *

SEQUENCE LISTING

```
<160> NUMBER OF SEQ ID NOS: 49

<210> SEQ ID NO 1
<211> LENGTH: 20
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 1
```

```
<223> OTHER INFORMATION: Xaa in position 1 is Lys or Arg
<220> FEATURE:
<221> NAME/KEY: VARIANT
<222> LOCATION: 2
<223> OTHER INFORMATION: Xaa in position 2 is Ala, Gly, Ser or Arg
<220> FEATURE:
<221> NAME/KEY: VARIANT
<222> LOCATION: 3
<223> OTHER INFORMATION: Xaa in position 3 is Leu or Met
<220> FEATURE:
<221> NAME/KEY: VARIANT
<222> LOCATION: 4
<223> OTHER INFORMATION: Xaa in position 4 is Gly or Arg
<220> FEATURE:
<221> NAME/KEY: VARIANT
<222> LOCATION: 5
<223> OTHER INFORMATION: Xaa in position 5 is Pro, Thr, Val, Ser, Gln or
      Ala
<220> FEATURE:
<221> NAME/KEY: VARIANT
<222> LOCATION: 6
<223> OTHER INFORMATION: Xaa in position 6 is Gly, Ala, Lys, Arg, Gln or
      Glu
<220> FEATURE:
<221> NAME/KEY: VARIANT
<222> LOCATION: 8
<223> OTHER INFORMATION: Xaa in position 8 is Thr or Ser
<220> FEATURE:
<221> NAME/KEY: VARIANT
<222> LOCATION: 9
<223> OTHER INFORMATION: Xaa in position 9 is Leu or Ile
<220> FEATURE:
<221> NAME/KEY: VARIANT
<222> LOCATION: 14
<223> OTHER INFORMATION: Xaa in position 14 is Thr, Ser or Val
<220> FEATURE:
<221> NAME/KEY: VARIANT
<222> LOCATION: 15
<223> OTHER INFORMATION: Xaa in position 15 is Ala or Ser
<220> FEATURE:
<221> NAME/KEY: VARIANT
<222> LOCATION: 16
<223> OTHER INFORMATION: Xaa in position 16 is Cys or Ser
<220> FEATURE:
<221> NAME/KEY: VARIANT
<222> LOCATION: 17
<223> OTHER INFORMATION: Xaa in position 17 is Gln or Leu
<220> FEATURE:
<221> NAME/KEY: VARIANT
<222> LOCATION: 18
<223> OTHER INFORMATION: Xaa in position 18 is Gly, Glu or Arg
<220> FEATURE:
<221> NAME/KEY: VARIANT
<222> LOCATION: 20
<223> OTHER INFORMATION: Xaa in position 20 is Gly or Arg

<400> SEQUENCE: 1

Xaa Xaa Xaa Xaa Xaa Xaa Ala Xaa Xaa Gln Thr Pro Trp Xaa Xaa Xaa
1               5                   10                  15

Xaa Xaa Val Xaa
            20

<210> SEQ ID NO 2
<211> LENGTH: 20
<212> TYPE: PRT
<213> ORGANISM: artificial sequence
<220> FEATURE:
<223> OTHER INFORMATION: synthetic peptide
<220> FEATURE:
<221> NAME/KEY: DISULFID
<222> LOCATION: 16
<223> OTHER INFORMATION: disulfide, optional, can form a homodimer with
      another SEQ ID NO 2 or a heterodimer with SEQ ID NO 5

<400> SEQUENCE: 2
```

-continued

```
Lys Ala Leu Gly Pro Gly Ala Thr Leu Gln Thr Pro Trp Thr Ala Cys
1               5                   10                  15

Gln Gly Val Gly
            20

<210> SEQ ID NO 3
<211> LENGTH: 20
<212> TYPE: PRT
<213> ORGANISM: artificial sequence
<220> FEATURE:
<223> OTHER INFORMATION: synthetic peptide

<400> SEQUENCE: 3

Arg Ala Leu Gly Pro Ala Ala Thr Leu Gln Thr Pro Trp Thr Ala Ser
1               5                   10                  15

Leu Gly Val Gly
            20

<210> SEQ ID NO 4
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 1
<223> OTHER INFORMATION: Xaa in position 1 is Arg, Lys, Asp or missing
<220> FEATURE:
<221> NAME/KEY: VARIANT
<222> LOCATION: 2
<223> OTHER INFORMATION: Xaa in position 2 is Trp, Gly, Lys or Arg
<220> FEATURE:
<221> NAME/KEY: VARIANT
<222> LOCATION: 3
<223> OTHER INFORMATION: Xaa in position 3 is Ile, Leu, Val or Met
<220> FEATURE:
<221> NAME/KEY: VARIANT
<222> LOCATION: 4
<223> OTHER INFORMATION: Xaa in position 4 is Ile, Val or Leu
<220> FEATURE:
<221> NAME/KEY: VARIANT
<222> LOCATION: 5
<223> OTHER INFORMATION: Xaa in position 5 is Leu, Met, Val or Pro
<220> FEATURE:
<221> NAME/KEY: VARIANT
<222> LOCATION: 12
<223> OTHER INFORMATION: Xaa in position 12 is  Gly or missing
<220> FEATURE:
<221> NAME/KEY: VARIANT
<222> LOCATION: 13
<223> OTHER INFORMATION: Xaa in position 13 is Gly or missing
<220> FEATURE:
<221> NAME/KEY: VARIANT
<222> LOCATION: 14
<223> OTHER INFORMATION: Xaa in position 14 is Gly or missing
<220> FEATURE:
<221> NAME/KEY: VARIANT
<222> LOCATION: 15
<223> OTHER INFORMATION: Xaa in position 15 is  Arg or Lys
<220> FEATURE:
<221> NAME/KEY: VARIANT
<222> LOCATION: 16
<223> OTHER INFORMATION: Xaa in position 16 is Met or Leu
<220> FEATURE:
<221> NAME/KEY: VARIANT
<222> LOCATION: 18
<223> OTHER INFORMATION: Xaa in position 18 is Ser, Cys or Gln
<220> FEATURE:
<221> NAME/KEY: VARIANT
<222> LOCATION: 20
<223> OTHER INFORMATION: Xaa in position 20 is Thr, Val, Ile, Ser or Ala
<220> FEATURE:
<221> NAME/KEY: VARIANT
```

```
<222> LOCATION: 21
<223> OTHER INFORMATION: Xaa in position 21 is Ser, Gly or Thr
<220> FEATURE:
<221> NAME/KEY: VARIANT
<222> LOCATION: 24
<223> OTHER INFORMATION: Xaa in position 24 is Asp, Glu, Cys or Gly
<220> FEATURE:
<221> NAME/KEY: VARIANT
<222> LOCATION: 25
<223> OTHER INFORMATION: Xaa in position 25 is Gly or missing

<400> SEQUENCE: 4

Xaa Xaa Xaa Xaa Xaa Gly Leu Asn Pro Leu Val Xaa Xaa Xaa Xaa Xaa
1               5                   10                  15

Tyr Xaa Pro Xaa Xaa Ile Leu Xaa Xaa
            20                  25

<210> SEQ ID NO 5
<211> LENGTH: 24
<212> TYPE: PRT
<213> ORGANISM: artificial sequence
<220> FEATURE:
<223> OTHER INFORMATION: synthetic peptide
<220> FEATURE:
<221> NAME/KEY: DISULFID
<222> LOCATION: 23
<223> OTHER INFORMATION: disulfide, optional, can form homodimer with
      another SEQ ID NO 5 or a heterodimer with SEQ ID NO 2

<400> SEQUENCE: 5

Trp Ile Ile Pro Gly Leu Asn Pro Leu Val Gly Gly Gly Lys Leu Tyr
1               5                   10                  15

Ser Pro Thr Ser Ile Leu Cys Gly
            20

<210> SEQ ID NO 6
<211> LENGTH: 24
<212> TYPE: PRT
<213> ORGANISM: artificial sequence
<220> FEATURE:
<223> OTHER INFORMATION: synthetic peptide

<400> SEQUENCE: 6

Arg Trp Leu Leu Leu Gly Leu Asn Pro Leu Val Gly Gly Gly Arg Leu
1               5                   10                  15

Tyr Ser Pro Thr Ser Ile Leu Gly
            20

<210> SEQ ID NO 7
<211> LENGTH: 23
<212> TYPE: PRT
<213> ORGANISM: artificial sequence
<220> FEATURE:
<223> OTHER INFORMATION: synthetic peptide

<400> SEQUENCE: 7

Lys Ile Leu Leu Gly Leu Asn Pro Leu Val Gly Gly Gly Arg Leu Tyr
1               5                   10                  15

Ser Pro Thr Ser Ile Leu Gly
            20

<210> SEQ ID NO 8
<211> LENGTH: 23
<212> TYPE: PRT
<213> ORGANISM: artificial sequence
<220> FEATURE:
<223> OTHER INFORMATION: synthetic peptide
```

<400> SEQUENCE: 8

Arg Leu Leu Leu Gly Leu Asn Pro Leu Val Gly Gly Gly Arg Leu Tyr
1               5                   10                  15

Ser Pro Thr Thr Ile Leu Gly
            20

<210> SEQ ID NO 9
<211> LENGTH: 27
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 1
<223> OTHER INFORMATION: Xaa in position 1 is Asn, Ser, Gly, His, Ala,
      Pro, Arg or missing
<220> FEATURE:
<221> NAME/KEY: VARIANT
<222> LOCATION: 2
<223> OTHER INFORMATION: Xaa in position 2 is Asn, Ala or Lys
<220> FEATURE:
<221> NAME/KEY: VARIANT
<222> LOCATION: 3
<223> OTHER INFORMATION: Xaa in position 3 is Pro, Gln, Gly, Ile or Leu
<220> FEATURE:
<221> NAME/KEY: VARIANT
<222> LOCATION: 7
<223> OTHER INFORMATION: Xaa in position 7 is Val or Ala
<220> FEATURE:
<221> NAME/KEY: VARIANT
<222> LOCATION: 8
<223> OTHER INFORMATION: Xaa in position 8 is Gly or Lys
<220> FEATURE:
<221> NAME/KEY: VARIANT
<222> LOCATION: 9
<223> OTHER INFORMATION: Xaa in position 9 is Glu, Asp, Lys, Phe or Thr
<220> FEATURE:
<221> NAME/KEY: VARIANT
<222> LOCATION: 10
<223> OTHER INFORMATION: Xaa in position 10 is Ile, Met, Val or Leu
<220> FEATURE:
<221> NAME/KEY: VARIANT
<222> LOCATION: 11
<223> OTHER INFORMATION: Xaa in position 11 is Tyr, Leu or missing
<220> FEATURE:
<221> NAME/KEY: VARIANT
<222> LOCATION: 12
<223> OTHER INFORMATION: Xaa in position 12 is Ser or missing
<220> FEATURE:
<221> NAME/KEY: VARIANT
<222> LOCATION: 14
<223> OTHER INFORMATION: Xaa in position 14 is Gly or missing
<220> FEATURE:
<221> NAME/KEY: VARIANT
<222> LOCATION: 15
<223> OTHER INFORMATION: Xaa in position 15 is Gly or missing
<220> FEATURE:
<221> NAME/KEY: VARIANT
<222> LOCATION: 16
<223> OTHER INFORMATION: Xaa in position 16 is Arg or missing
<220> FEATURE:
<221> NAME/KEY: VARIANT
<222> LOCATION: 17
<223> OTHER INFORMATION: Xaa in position 17 is Asp, Arg, Trp, Ala or
      missing
<220> FEATURE:
<221> NAME/KEY: VARIANT
<222> LOCATION: 18
<223> OTHER INFORMATION: Xaa in position 18 is Ile or missing
<220> FEATURE:
<221> NAME/KEY: VARIANT
<222> LOCATION: 19
<223> OTHER INFORMATION: Xaa in position 19 is Tyr or missing
<220> FEATURE:

```
<221> NAME/KEY: VARIANT
<222> LOCATION: 20
<223> OTHER INFORMATION: Xaa in position 20 is Lys or Arg
<220> FEATURE:
<221> NAME/KEY: VARIANT
<222> LOCATION: 21
<223> OTHER INFORMATION: Xaa in position 21 is Arg, Lys or Asp
<220> FEATURE:
<221> NAME/KEY: VARIANT
<222> LOCATION: 22
<223> OTHER INFORMATION: Xaa in position 22 is Trp or Gly
<220> FEATURE:
<221> NAME/KEY: VARIANT
<222> LOCATION: 23
<223> OTHER INFORMATION: Xaa in position 23 is Ile, Met, Val, Gln or Ala
<220> FEATURE:
<221> NAME/KEY: VARIANT
<222> LOCATION: 24
<223> OTHER INFORMATION: Xaa in position 24 is Ile, Val or Ala
<220> FEATURE:
<221> NAME/KEY: VARIANT
<222> LOCATION: 25
<223> OTHER INFORMATION: Xaa in position 25 is Leu, Met or Val
<220> FEATURE:
<221> NAME/KEY: VARIANT
<222> LOCATION: 26
<223> OTHER INFORMATION: Xaa in position 26 is Gly or Cys
<220> FEATURE:
<221> NAME/KEY: VARIANT
<222> LOCATION: 27
<223> OTHER INFORMATION: Xaa in position 27 is Leu or missing

<400> SEQUENCE: 9

Xaa Xaa Xaa Pro Ile Pro Xaa Xaa Xaa Xaa Xaa Xaa Gly Xaa Xaa Xaa
1               5                   10                  15

Xaa Xaa Xaa Xaa Xaa Xaa Xaa Xaa Xaa Xaa Xaa
            20                  25

<210> SEQ ID NO 10
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: DISULFID
<222> LOCATION: 24
<223> OTHER INFORMATION: disulfide, optional

<400> SEQUENCE: 10

Arg Asn Ile Pro Ile Pro Val Gly Asp Ile Tyr Gly Gly Gly Asp Ile
1               5                   10                  15

Tyr Lys Arg Trp Gln Ala Leu Cys Leu
            20                  25

<210> SEQ ID NO 11
<211> LENGTH: 26
<212> TYPE: PRT
<213> ORGANISM: artificial sequence
<220> FEATURE:
<223> OTHER INFORMATION: synthetic peptide

<400> SEQUENCE: 11

Arg Ala Ile Pro Ile Pro Ala Gly Thr Leu Leu Ser Gly Gly Gly Arg
1               5                   10                  15

Ala Ile Tyr Lys Arg Trp Ala Ile Leu Gly
            20                  25

<210> SEQ ID NO 12
<211> LENGTH: 23
```

```
<212> TYPE: PRT
<213> ORGANISM: artificial sequence
<220> FEATURE:
<223> OTHER INFORMATION: synthetic peptide

<400> SEQUENCE: 12

Ala Leu Pro Ile Pro Ala Gly Phe Ile Tyr Gly Gly Gly Arg Ile Tyr
1               5                   10                  15

Lys Arg Trp Gln Ala Leu Gly
            20

<210> SEQ ID NO 13
<211> LENGTH: 22
<212> TYPE: PRT
<213> ORGANISM: artificial sequence
<220> FEATURE:
<223> OTHER INFORMATION: synthetic peptide

<400> SEQUENCE: 13

Lys Ile Pro Ile Pro Val Gly Phe Ile Gly Gly Gly Trp Ile Tyr Lys
1               5                   10                  15

Arg Trp Ala Ile Leu Gly
            20

<210> SEQ ID NO 14
<211> LENGTH: 24
<212> TYPE: PRT
<213> ORGANISM: artificial sequence
<220> FEATURE:
<223> OTHER INFORMATION: synthetic peptide

<400> SEQUENCE: 14

Lys Ile Pro Ile Pro Val Gly Thr Leu Leu Ser Gly Gly Gly Arg Ile
1               5                   10                  15

Tyr Lys Arg Trp Ala Ile Leu Gly
            20

<210> SEQ ID NO 15
<211> LENGTH: 31
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 1
<223> OTHER INFORMATION: Xaa in position 1 is Pro, Lys, Arg or missing
<220> FEATURE:
<221> NAME/KEY: VARIANT
<222> LOCATION: 2
<223> OTHER INFORMATION: Xaa in position 2 is Glu, Arg, Phe or Lys
<220> FEATURE:
<221> NAME/KEY: VARIANT
<222> LOCATION: 5
<223> OTHER INFORMATION: Xaa in position 5 is Pro or Thr
<220> FEATURE:
<221> NAME/KEY: VARIANT
<222> LOCATION: 6
<223> OTHER INFORMATION: Xaa in position 6 is Met, Thr or Nle
<220> FEATURE:
<221> NAME/KEY: VARIANT
<222> LOCATION: 7
<223> OTHER INFORMATION: Xaa in position 7 is Phe or Leu
<220> FEATURE:
<221> NAME/KEY: VARIANT
<222> LOCATION: 8
<223> OTHER INFORMATION: Xaa in position 8 is Ser, Thr, Ala or Met
<220> FEATURE:
<221> NAME/KEY: VARIANT
<222> LOCATION: 9
```

```
<223> OTHER INFORMATION: Xaa in position 9 is Ala, Glu or Leu
<220> FEATURE:
<221> NAME/KEY: VARIANT
<222> LOCATION: 11
<223> OTHER INFORMATION: Xaa in position 11 is Ser or missing
<220> FEATURE:
<221> NAME/KEY: VARIANT
<222> LOCATION: 13
<223> OTHER INFORMATION: Xaa in position 13 is Gly or missing
<220> FEATURE:
<221> NAME/KEY: VARIANT
<222> LOCATION: 14
<223> OTHER INFORMATION: Xaa in position 14 is Gly or missing
<220> FEATURE:
<221> NAME/KEY: VARIANT
<222> LOCATION: 15
<223> OTHER INFORMATION: Xaa in position 15 is Arg or missing
<220> FEATURE:
<221> NAME/KEY: VARIANT
<222> LOCATION: 16
<223> OTHER INFORMATION: Xaa in position 16 is Arg or missing
<220> FEATURE:
<221> NAME/KEY: VARIANT
<222> LOCATION: 17
<223> OTHER INFORMATION: Xaa in position 17 is Arg or missing
<220> FEATURE:
<221> NAME/KEY: VARIANT
<222> LOCATION: 18
<223> OTHER INFORMATION: Xaa in position 18 is Ala, Arg or missing
<220> FEATURE:
<221> NAME/KEY: VARIANT
<222> LOCATION: 19
<223> OTHER INFORMATION: Xaa in position 19 is Ile, Leu or missing
<220> FEATURE:
<221> NAME/KEY: VARIANT
<222> LOCATION: 20
<223> OTHER INFORMATION: Xaa in position 20 is Ser, Ala, Leu or missing
<220> FEATURE:
<221> NAME/KEY: VARIANT
<222> LOCATION: 21
<223> OTHER INFORMATION: Xaa in position 21 is Tyr, Glu or Asp
<220> FEATURE:
<221> NAME/KEY: VARIANT
<222> LOCATION: 22
<223> OTHER INFORMATION: Xaa in position 22 is Gly or Asp
<220> FEATURE:
<221> NAME/KEY: VARIANT
<222> LOCATION: 23
<223> OTHER INFORMATION: Xaa in position 23 is Ala or Leu
<220> FEATURE:
<221> NAME/KEY: VARIANT
<222> LOCATION: 24
<223> OTHER INFORMATION: Xaa in position 24 is Thr, Ile, Val, Leu or Asn
<220> FEATURE:
<221> NAME/KEY: VARIANT
<222> LOCATION: 25
<223> OTHER INFORMATION: Xaa in position 25 is Pro, Thr or Ser
<220> FEATURE:
<221> NAME/KEY: VARIANT
<222> LOCATION: 26
<223> OTHER INFORMATION: Xaa in position 26 is Tyr, Phe, Nle, His or Gln
<220> FEATURE:
<221> NAME/KEY: VARIANT
<222> LOCATION: 27
<223> OTHER INFORMATION: Xaa in position 27 is Asp, Asn, Leu or Ala
<220> FEATURE:
<221> NAME/KEY: VARIANT
<222> LOCATION: 28
<223> OTHER INFORMATION: Xaa in position 28 is Leu, Ile, Val or Asn
<220> FEATURE:
<221> NAME/KEY: VARIANT
<222> LOCATION: 29
<223> OTHER INFORMATION: Xaa in position 29 is Asn, Tyr, Cys or Gly
<220> FEATURE:
<221> NAME/KEY: VARIANT
<222> LOCATION: 30
<223> OTHER INFORMATION: Xaa in position 30 is Thr, Met, Ile, Ala, Val
      or missing
<220> FEATURE:
```

```
<221> NAME/KEY: VARIANT
<222> LOCATION: 31
<223> OTHER INFORMATION: Xaa in position 31 is Gly or missing

<400> SEQUENCE: 15

Xaa Xaa Ile Ile Xaa Xaa Xaa Xaa Xaa Leu Xaa Gly Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 16
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 6
<223> OTHER INFORMATION: Xaa is Nle
<220> FEATURE:
<221> NAME/KEY: VARIANT
<222> LOCATION: 21
<223> OTHER INFORMATION: Xaa is Nle
<220> FEATURE:
<221> NAME/KEY: DISULFID
<222> LOCATION: 24
<223> OTHER INFORMATION: disulfide, optional

<400> SEQUENCE: 16

Lys Phe Ile Ile Pro Xaa Phe Ser Ala Leu Gly Gly Ala Ile Ser Tyr
1               5                   10                  15

Asp Leu Asn Thr Xaa Leu Asn Cys Ile
            20                  25

<210> SEQ ID NO 17
<211> LENGTH: 28
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 6
<223> OTHER INFORMATION: Xaa is Nle
<220> FEATURE:
<221> NAME/KEY: DISULFID
<222> LOCATION: 26
<223> OTHER INFORMATION: disulfide, optional

<400> SEQUENCE: 17

Lys Phe Ile Ile Pro Xaa Phe Ser Ala Leu Ser Gly Gly Gly Ala Ile
1               5                   10                  15

Ser Tyr Asp Leu Asn Thr Phe Leu Asn Cys Ile Gly
            20                  25

<210> SEQ ID NO 18
<211> LENGTH: 27
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 6
<223> OTHER INFORMATION: Xaa is Nle

<400> SEQUENCE: 18

Arg Phe Ile Ile Pro Xaa Phe Thr Ala Leu Ser Gly Gly Arg Arg Ala
```

```
1               5                  10                  15
Leu Leu Tyr Gly Ala Thr Pro Tyr Ala Ile Gly
            20                  25

<210> SEQ ID NO 19
<211> LENGTH: 24
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 5
<223> OTHER INFORMATION: Xaa is Nle

<400> SEQUENCE: 19

Lys Ile Ile Pro Xaa Phe Ser Ala Leu Gly Gly Gly Arg Leu Leu Tyr
1               5                   10                  15
Gly Ala Thr Pro Tyr Ala Ile Gly
            20

<210> SEQ ID NO 20
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 5
<223> OTHER INFORMATION: Xaa is Nle

<400> SEQUENCE: 20

Arg Ile Ile Pro Xaa Phe Thr Ala Leu Ser Gly Gly Gly Arg Leu Leu
1               5                   10                  15
Tyr Gly Ala Thr Pro Tyr Ala Ile Gly
            20                  25

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24
<211> LENGTH: 24
<212> TYPE: PRT
<213> ORGANISM: artificial sequence
<220> FEATURE:
<223> OTHER INFORMATION: synthetic peptide
<220> FEATURE:
<221> NAME/KEY: DISULFID
<222> LOCATION: 23
<223> OTHER INFORMATION: disulfide, optional

<400> SEQUENCE: 24
```

```
Asn Ile Pro Ile Pro Val Gly Asp Ile Tyr Gly Gly Gly Asp Ile Tyr
1               5                   10                  15

Lys Arg Tyr Gln Ala Leu Cys Leu
            20

<210> SEQ ID NO 25
<211> LENGTH: 24
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: 5
<223> OTHER INFORMATION: Xaa is Nle
<220> FEATURE:
<221> NAME/KEY: VARIANT
<222> LOCATION: 20
<223> OTHER INFORMATION: Xaa is Nle
<220> FEATURE:
<221> NAME/KEY: DISULFID
<222> LOCATION: 23
<223> OTHER INFORMATION: disulfide, optional

<400> SEQUENCE: 25

Trp Ile Ile Pro Xaa Phe Ser Ala Leu Gly Gly Ala Ile Ser Tyr Asp
1               5                   10                  15

Leu Asn Thr Xaa Leu Asn Cys Ile
            20

<210> SEQ ID NO 26
<211> LENGTH: 20
<212> TYPE: PRT
<213> ORGANISM: Homo sapiens

<400> SEQUENCE: 26

Lys Ala Leu Gly Pro Gly Ala Thr Leu Glu Glu Met Met Thr Ala Cys
1               5                   10                  15

Gln Gly Val Gly
            20

<210> SEQ ID NO 27
<211> LENGTH: 20
<212> TYPE: PRT
<213> ORGANISM: Homo sapiens

<400> SEQUENCE: 27

Arg Arg Met Arg Thr Lys Ala Ser Ile Lys Asp Met Leu Ser Ser Ser
1               5                   10                  15

Gln Arg Val Arg
            20

<210> SEQ ID NO 28
<211> LENGTH: 20
<212> TYPE: PRT
<213> ORGANISM: Homo sapiens

<400> SEQUENCE: 28

Lys Gly Leu Gly Val Arg Ala Thr Leu Glu Glu Met Met Val Ala Cys
1               5                   10                  15

Gln Gly Val Gly
            20

<210> SEQ ID NO 29
```

```
<211> LENGTH: 20
<212> TYPE: PRT
<213> ORGANISM: Homo sapiens

<400> SEQUENCE: 29

Lys Ser Leu Gly Ala Ala Ala Thr Leu Glu Glu Met Met Thr Ala Cys
1               5                   10                  15

Gln Gly Val Gly
            20

<210> SEQ ID NO 30
<211> LENGTH: 20
<212> TYPE: PRT
<213> ORGANISM: Homo sapiens

<400> SEQUENCE: 30

Lys Ala Leu Gly Ser Glu Ala Thr Leu Glu Glu Met Met Thr Ala Cys
1               5                   10                  15

Gln Gly Val Gly
            20

<210> SEQ ID NO 31
<211> LENGTH: 20
<212> TYPE: PRT
<213> ORGANISM: Homo sapiens

<400> SEQUENCE: 31

Lys Ala Leu Gly Gln Gln Ala Thr Leu Glu Glu Met Met Thr Ala Cys
1               5                   10                  15

Gln Gly Val Gly
            20

<210> SEQ ID NO 32
<211> LENGTH: 29
<212> TYPE: PRT
<213> ORGANISM: artificial sequence
<220> FEATURE:
<223> OTHER INFORMATION: synthetic peptide
<220> FEATURE:
<221> NAME/KEY: DISULFID
<222> LOCATION: 5
<223> OTHER INFORMATION: disulfide
<220> FEATURE:
<221> NAME/KEY: VARIANT
<222> LOCATION: 21
<223> OTHER INFORMATION: Xaa is 2-aminohexanoic acid
<220> FEATURE:
<221> NAME/KEY: VARIANT
<222> LOCATION: 22
<223> OTHER INFORMATION: Xaa is 2-aminohexanoic acid
<220> FEATURE:
<221> NAME/KEY: DISULFID
<222> LOCATION: 25
<223> OTHER INFORMATION: disulfide

<400> SEQUENCE: 32

Ala Asn Pro Asp Cys Lys Gln Ile Leu Lys Ser leu Gly Pro Gly Ala
1               5                   10                  15

Thr Leu Gln Gln Xaa Xaa Thr Ala Cys Gln Gly Val Gly
            20                  25

<210> SEQ ID NO 33
<211> LENGTH: 18
<212> TYPE: PRT
<213> ORGANISM: artificial sequence
<220> FEATURE:
<223> OTHER INFORMATION: synthetic peptide
```

```
<220> FEATURE:
<221> NAME/KEY: DISULFID
<222> LOCATION: 7
<223> OTHER INFORMATION: disulfide
<220> FEATURE:
<221> NAME/KEY: VARIANT
<222> LOCATION: 11
<223> OTHER INFORMATION: Xaa is 2-aminohexanoic acid
<220> FEATURE:
<221> NAME/KEY: DISULFID
<222> LOCATION: 14
<223> OTHER INFORMATION: disulfide

<400> SEQUENCE: 33

Leu Ile Trp Gly Ala Thr Cys Gln Glu His Xaa Thr Ala Cys Gln Gly
1               5                   10                  15

Val Gly

<210> SEQ ID NO 34
<211> LENGTH: 21
<212> TYPE: PRT
<213> ORGANISM: Homo sapiens

<400> SEQUENCE: 34

Arg Trp Ile Ile Leu Gly Leu Asn Lys Ile Val Arg Met Tyr Ser Pro
1               5                   10                  15

Thr Ser Ile Leu Asp
            20

<210> SEQ ID NO 35
<211> LENGTH: 21
<212> TYPE: PRT
<213> ORGANISM: Homo sapiens

<400> SEQUENCE: 35

Lys Gly Val Val Met Gly Leu Asn Lys Met Val Lys Met Tyr Cys Pro
1               5                   10                  15

Val Gly Ile Leu Glu
            20

<210> SEQ ID NO 36
<211> LENGTH: 21
<212> TYPE: PRT
<213> ORGANISM: Homo sapiens

<400> SEQUENCE: 36

Lys Trp Met Ile Val Gly Leu Asn Lys Val Val Arg Met Tyr Gln Pro
1               5                   10                  15

Ile Ser Ile Leu Gly
            20

<210> SEQ ID NO 37
<211> LENGTH: 21
<212> TYPE: PRT
<213> ORGANISM: Homo sapiens

<400> SEQUENCE: 37

Arg Trp Ile Ile Leu Gly Leu Asn Lys Ile Val Arg Met Tyr Ser Pro
1               5                   10                  15

Ser Ser Ile Leu Asp
            20

<210> SEQ ID NO 38
<211> LENGTH: 21
```

```
<212> TYPE: PRT
<213> ORGANISM: Homo sapiens

<400> SEQUENCE: 38

Arg Trp Ile Ile Leu Gly Leu Asn Lys Ile Val Arg Met Tyr Ser Pro
1               5                   10                  15

Ala Ser Ile Leu Asp
            20

<210> SEQ ID NO 39
<211> LENGTH: 19
<212> TYPE: PRT
<213> ORGANISM: Homo sapiens

<400> SEQUENCE: 39

Asn Asn Pro Pro Ile Pro Val Gly Glu Ile Tyr Lys Arg Trp Ile Ile
1               5                   10                  15

Leu Gly Leu

<210> SEQ ID NO 40
<211> LENGTH: 19
<212> TYPE: PRT
<213> ORGANISM: Homo sapiens

<400> SEQUENCE: 40

Ser Asn Gln Ala Val Pro Val Lys Asp Met Leu Arg Lys Gly Met Val
1               5                   10                  15

Met Gly Leu

<210> SEQ ID NO 41
<211> LENGTH: 19
<212> TYPE: PRT
<213> ORGANISM: Homo sapiens

<400> SEQUENCE: 41

Gly Asn Gly Ser Asn Pro Val Gly Lys Val Tyr Lys Asp Trp Val Ile
1               5                   10                  15

Val Gly Leu

<210> SEQ ID NO 42
<211> LENGTH: 19
<212> TYPE: PRT
<213> ORGANISM: Homo sapiens

<400> SEQUENCE: 42

His Asn Pro Gly Thr Pro Val Gly Glu Ile Tyr Lys Arg Trp Ile Ile
1               5                   10                  15

Leu Gly Leu

<210> SEQ ID NO 43
<211> LENGTH: 19
<212> TYPE: PRT
<213> ORGANISM: Homo sapiens

<400> SEQUENCE: 43

Ala Asn Pro Pro Ile Pro Val Gly Glu Ile Tyr Lys Arg Trp Ile Ile
1               5                   10                  15

Leu Gly Leu

<210> SEQ ID NO 44
<211> LENGTH: 19
```

```
<212> TYPE: PRT
<213> ORGANISM: Homo sapiens

<400> SEQUENCE: 44

Pro Asn Pro Pro Ile Pro Val Gly Glu Ile Tyr Lys Arg Trp Ile Ile
1               5                   10                  15

Leu Gly Leu

<210> SEQ ID NO 45
<211> LENGTH: 21
<212> TYPE: PRT
<213> ORGANISM: Homo sapiens

<400> SEQUENCE: 45

Pro Glu Val Ile Pro Met Phe Ser Ala Leu Ser Glu Gly Ala Thr Pro
1               5                   10                  15

Gln Asp Leu Asn Thr
            20

<210> SEQ ID NO 46
<211> LENGTH: 21
<212> TYPE: PRT
<213> ORGANISM: Homo sapiens

<400> SEQUENCE: 46

Pro Arg Ile Thr Thr Thr Leu Thr Glu Leu Ala Asp Gly Ala Ile Ser
1               5                   10                  15

Tyr Asn Ile Tyr Met
            20

<210> SEQ ID NO 47
<211> LENGTH: 21
<212> TYPE: PRT
<213> ORGANISM: Homo sapiens

<400> SEQUENCE: 47

Pro Glu Leu Asn Pro Met Phe Ala Leu Leu Ser Glu Gly Ala Val Pro
1               5                   10                  15

His Asp Val Asn Ile
            20

<210> SEQ ID NO 48
<211> LENGTH: 21
<212> TYPE: PRT
<213> ORGANISM: Homo sapiens

<400> SEQUENCE: 48

Pro Glu Val Ile Pro Met Phe Met Ala Leu Ser Glu Gly Ala Leu Pro
1               5                   10                  15

Gln Asp Leu Asn Ala
            20

<210> SEQ ID NO 49
<211> LENGTH: 21
<212> TYPE: PRT
<213> ORGANISM: Homo sapiens
```

```
<400> SEQUENCE: 49

Pro Glu Val Ile Pro Met Phe Ser Ala Leu Ser Glu Gly Ala Thr Pro
1               5                   10                  15

Gln Asp Leu Asn Val
            20
```